United States Patent
Latif

(10) Patent No.: US 10,258,750 B2
(45) Date of Patent: Apr. 16, 2019

(54) DAMAGE-INDICATING MEDICAL CANNULA

(71) Applicant: KLOSE Monitoring, LLC, Bartlett, TN (US)

(72) Inventor: Kashif Latif, Bartlett, TN (US)

(73) Assignee: KLOSE Monitoring, LLC, Bartlett, TN (US)

( * ) Notice: Subject to any disclaimer, the term of this patent is extended or adjusted under 35 U.S.C. 154(b) by 145 days.

(21) Appl. No.: 15/353,195

(22) Filed: Nov. 16, 2016

(65) Prior Publication Data

US 2018/0133412 A1    May 17, 2018

(51) Int. Cl.
*A61M 5/50* (2006.01)
*A61M 5/32* (2006.01)
*A61M 5/158* (2006.01)

(52) U.S. Cl.
CPC .......... *A61M 5/5086* (2013.01); *A61M 5/158* (2013.01); *A61M 5/32* (2013.01)

(58) Field of Classification Search
CPC ............................ A61M 5/5086; A61M 5/158
USPC ....... 200/203, 211, 212, 264, 265, 266, 273; 138/204
See application file for complete search history.

(56) References Cited

U.S. PATENT DOCUMENTS

| | | |
|---|---|---|
| 3,647,504 A | 3/1972 | Hayes, Jr. et al. |
| 5,248,299 A | 9/1993 | Ota |
| 5,797,869 A | 8/1998 | Martin et al. |
| 7,762,253 B2 | 7/2010 | Acker et al. |
| 2004/0065377 A1 | 4/2004 | Whiteley |
| 2007/0131297 A1 | 6/2007 | Spaolonzi et al. |
| 2009/0314097 A1 | 12/2009 | Cairo |
| 2013/0061971 A1 | 3/2013 | Chamberland |
| 2013/0220466 A1 | 8/2013 | Zadiyeh et al. |
| 2013/0284296 A1 | 10/2013 | Berger et al. |
| 2014/0150710 A1 | 6/2014 | Jones et al. |
| 2015/0080857 A1 | 3/2015 | Stroup et al. |
| 2015/0083265 A1* | 3/2015 | Waldrip .................. F21V 33/00 138/146 |
| 2015/0153006 A1 | 6/2015 | Nieminen |
| 2016/0256667 A1 | 9/2016 | Ribelin et al. |

* cited by examiner

*Primary Examiner* — Amber R Stiles
(74) *Attorney, Agent, or Firm* — Fish & Richardson P.C.

(57) ABSTRACT

An example medical device includes a body portion having a tubular inner wall defining an inner channel, and a tubular outer wall encircling the inner wall. The outer wall defines an outer channel between the outer wall and the inner wall. The body portion also includes an indicator substance disposed within the outer channel. The device also includes an indicator portion defining an indicator channel. The body portion is configured to insert at least in part into a patient, and the indicator portion is configured to remain at least in part along an exterior of the patient when the body portion is inserted into the patient. The device is also configured to transfer at least a portion of the indicator substance from the outer channel to the indicator channel when the body portion is bent.

16 Claims, 12 Drawing Sheets

DAMAGE-INDICATING MEDICAL CANNULA

TECHNICAL FIELD

This disclosure relates to medical cannulas.

BACKGROUND

A medical cannula is a tube-like device that can be inserted into the body of a patient, often for the delivery of fluid into the patient or the removal of fluid from the patient. As an example, a user can attach one end of a medical cannula to a vessel containing a therapeutic substance (e.g., a container of an insulin solution), and insert the opposite end of the medical cannula into a patient's body (e.g., by pressing a tip of the cannula against the patient's body until it pierces the patient's skin). This creates a fluid pathway between the vessel and the interior of the patient's body, and facilitates administration of the therapeutic substance.

During use, a medical cannula may be bent or "kinked." For example, when the tip of the medical cannula is pressed against the patient's body, the tip may be deflected by the patient's body (e.g., the patient's skin or structures under the patient's skin). As a result, the medical cannula may be bent, resulting in the crimping and obstruction of the cannula's inner channel. This can interfere with the flow of fluid into or out of the patient, and can negatively impact the patient's treatment.

In some cases, it is difficult for a user to visually ascertain whether a medical cannula is bent or kinked. For example, the tip of the medical cannula may be obscured when it is pressed against the user's body (e.g., by other structures of the medical cannula, objects attached the medical cannula, the patient's body, and so forth). Thus, in some cases, a user may have difficulty determining whether therapeutic substances are being properly administered to a patient.

SUMMARY

Implementations of a damage-indicating medical cannula are described herein. Implementations of the medical cannula enable a user to visually ascertain whether a cannula has been bent or kinked during insertion or use. This is beneficial, for example, as it enables the user and/or patient to efficiently identify and replace a faulty medical cannula, such that the patient's quality of care is not negatively impacted.

In general, in an aspect, a medical device includes medical device a body portion having a tubular inner wall defining an inner channel, and a tubular outer wall encircling the inner wall. The outer wall defines an outer channel between the outer wall and the inner wall. The device also includes an indicator substance disposed within the outer channel. The device also includes an indicator portion defining an indicator channel. The body portion is configured to insert at least in part into a patient, and the indicator portion is configured to remain at least in part along an exterior of the patient when the body portion is inserted into the patient. The device is also configured to transfer at least a portion of the indicator substance from the outer channel to the indicator channel when the body portion is bent.

Implementations of this aspect can include one or more of the following features.

In some implementations, the outer channel and the indicator channel can be separated by a frangible membrane, and the frangible membrane can be configured to rupture when the body portion is bent.

In some implementations, the indicator channel and the outer channel can be in fluid communication upon rupture of the frangible membrane.

In some implementations, the indicator portion can include a transparent or translucent surface, and an interior of the indicator channel can be visible through the transparent or translucent surface when the body portion is inserted into the patient.

In some implementations, the indicator substance can include a colored dye.

In some implementations, the indicator channel can contain a reactive substance. Transferring at least the portion of the indicator substance from the outer channel to the indicator channel can cause a reaction between the indicator substance and the reactive substance.

In some implementations, the reaction can cause the indicator substance to change color.

In some implementations, the indicator portion can be disposed along a first end of the outer channel.

In some implementations, the indicator portion can be disc shaped.

In some implementations, the device can further include an adapter portion. The adapter portion can define an access channel through the inner wall and the outer wall. The access channel can be in fluid communication with the inner channel.

In some implementations, the adapter portion can be configured to physically couple to a vessel containing a fluid. The device can be configured to deliver the fluid from the vessel to the patient through the access channel and the inner channel.

In some implementations, the fluid can include insulin.

In some implementations, the device can further include a reservoir containing a fluid. The reservoir can be in fluid communication with the inner channel.

In some implementations, the fluid can include insulin.

In some implementations, the device can further include an interface material positioned within the indicator channel.

In some implementations, the interface material can be a sponge.

In general, in another aspect, a medical device includes a body portion having a tubular inner wall defining an inner channel, and a tubular outer wall encircling the inner wall. The outer wall defines an outer channel between the outer wall and the inner wall. The device also includes an indicator substance disposed within the outer channel. The body portion is configured to insert at least in part into a patient, and the device is configured to release at least a portion of the indicator substance from the outer channel to an exterior of the medical device when the body portion is bent.

Implementations of this aspect can include one or more of the following features.

In some implementations, the indicator substance can be an irritant.

In some implementations, the outer wall can be configured to rupture when the body portion is bent.

In general, in another aspect, a medical device includes a body portion having a tubular wall defining an inner channel, a first layer affixed to the wall, and a second layer affixed to the first layer. The device also includes an electronic control module in electrical communication with the first layer. The body portion is configured to insert at least in part into a patient, and the second layer is configured to rupture when the body portion is bent to expose the first layer to an exterior of the medical device. The first layer is configured to generate an electrical response upon contacting a interstitial fluid in an environment surrounding the medical device, and the electronic control module is configured to detect the electrical response and generate an indication to a user based on the detected electrical response.

The details of one or more embodiments are set forth in the accompanying drawings and the description below. Other features and advantages will be apparent from the description and drawings, and from the claims.

DETAILED DESCRIPTION

Implementations of a damage-indicating medical cannula are described herein. Implementations of the medical cannula enable a user to visually ascertain whether a cannula has been bent or kinked during insertion or use. In some cases, implementations of the medical cannula can be used to deliver a therapeutic substance (e.g., an insulin solution) to an interior of a patient, and enable a user to visually determine whether the therapeutic substance is being properly delivered. In some cases, implementations of the medical cannula can also provide tactile feedback to the patient and/or transmit electronic messages when it has been bent or kinked. This is beneficial, for example, as it enables the user and/or patient to efficiently identity and replace a faulty medical cannula, such that the patient's quality of care is not negatively impacted.

Figure 1:
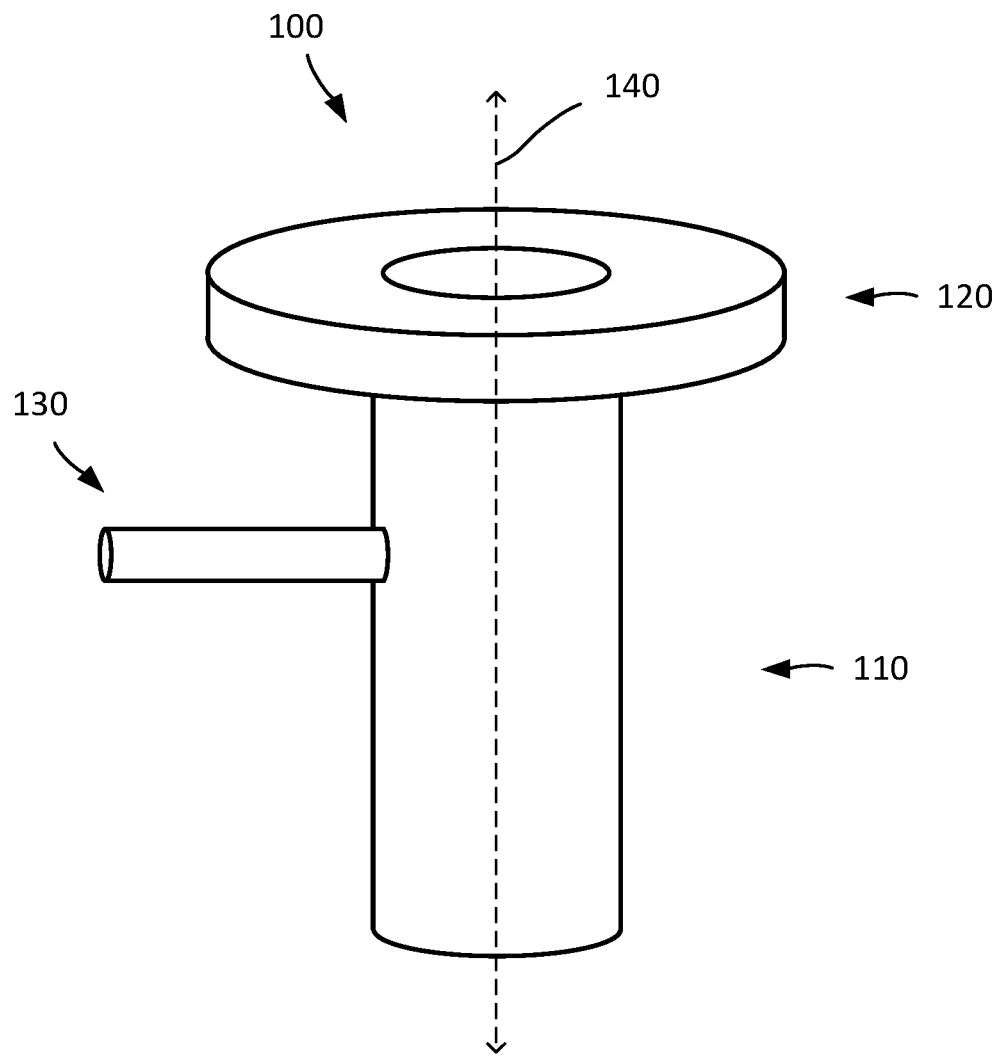
FIG. 1 is a diagram of an example medical cannula.

An example implementation of a damage-indicating medical cannula 100 is shown in FIG. 1. The medical cannula 100 includes a body portion 110, an indicator portion 120, and an adapter portion 130. In this example, the body portion 110 extends along an axis of extension 140, and the indicator portion 120 is disposed atop the body portion 110 along the axis of extension 140. The adapter portion 130 protrudes from the body portion 110 (e.g., in a direction approximately orthogonal to the axis of extension 140).

Figure 2A:
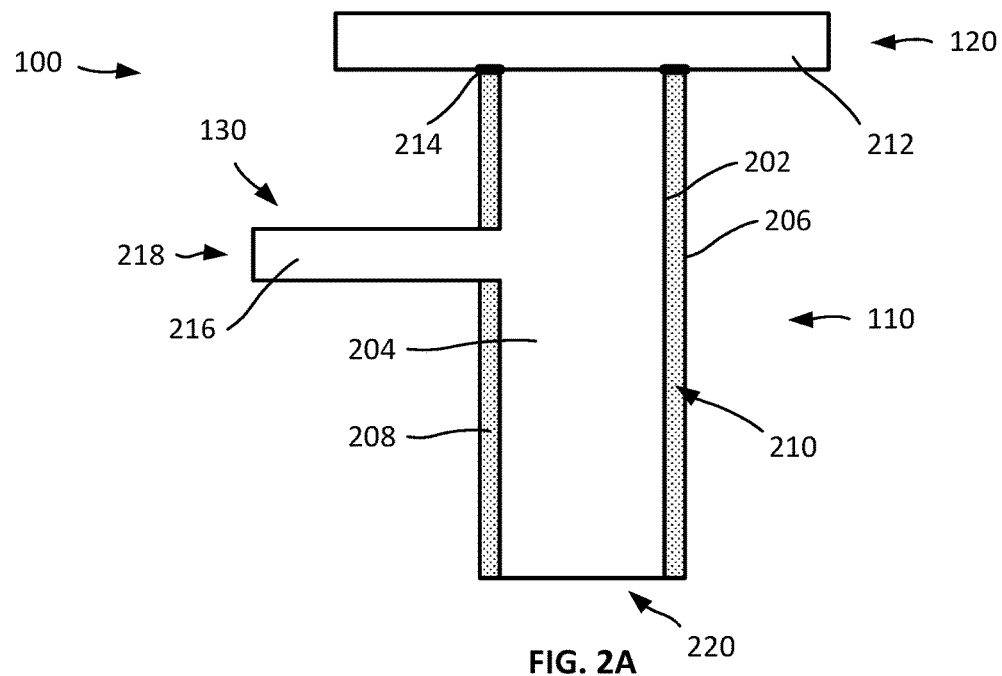
FIGS. 2A and 2B are diagrams depicting the use of an example medical cannula.

FIG. 2A shows a cross-section of the medical cannula 100 along a plane parallel of the axis of extension 140.

The body portion 110 is generally tubular in shape. The body portion 110 includes a tubular inner wall 202 that defines an inner channel 204. The body portion also includes a tubular outer wall 206 that encircles the inner wall 202, such that an annular outer channel 208 is defined between the inner wall 202 and the outer wall 206. The inner channel 204 and the outer channel 208 are in fluid isolation with respect to one another, such that the contents of the inner channel 204 and the outer channel 208 do not mix.

The outer channel 208 contains an indicator substance 210. In the example shown in FIG. 2A, the indicator substance 210 is a colored dye (e.g., a solution having a visually discernable color, such as red, green, blue, black, or any other color). However, the indicator substance 210 need not be colored. As the inner channel 204 and the outer channel 208 are in fluid isolation with respect to one another, the indicator substance 210 is securely contained within the outer channel 208, and cannot escape into the inner channel 204.

The indicator portion 120 is generally disc-like in shape, and is positioned above the body portion 110. The indicator portion 120 defines an indicator channel 212. The indicator channel 212 and the outer channel 208 are separated by an annular frangible membrane 214. When the frangible membrane 214 is intact, the indicator channel 212 and the outer channel 208 are in fluid isolation with respect to one another, such that the contents of the indicator channel 212 and the outer channel 208 do not mix. In some cases, the indicator channel 212 contains air or is a vacuum. In some cases, the indicator channel 212 contains a fluid having a different color than that of the indicator substance 210 (e.g., a clear fluid, a white fluid, or some other contrasting color). In some cases, the indicator channel 212 contains a fluid-sensitive material, such as a paper, sponge, or other material that changes color when contacted by a fluid (e.g., the indicator substance 210).

The adapter portion 130 protrudes from the body portion 110, and defines an adapter channel 216 that is in fluid communication with the inner channel 204. Fluids introduced into a receiving end 218 of the adapter portion 130 are guided to the exit end 220 of the body portion 110.

Figure 2B:
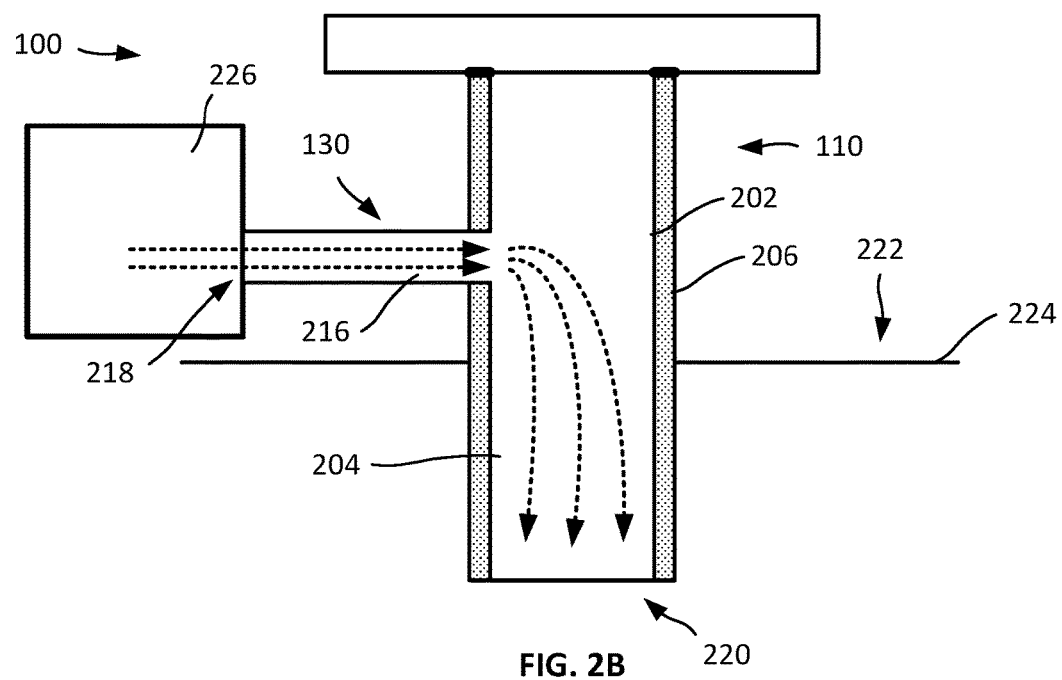

The medical cannula 100 can be used to deliver a fluid (e.g., a therapeutic substance, such as an insulin solution) into a patient. To illustrate, FIG. 2B shows the medical cannula 100 inserted into a patient's body 222. The medical cannula 100 can be inserted, for example, by pressing the medical cannula 100 against the patient's body 222, such that the exit end 220 of the body portion 110 pierces the patient's skin 224. In some cases, the edges of the exit end 220 can be sharpened or beveled to facilitate insertion into the patient's body 222.

The receiving end 218 is attached to a vessel 226 containing a fluid (e.g., a container of a therapeutic substance, such as an insulin solution). Accordingly, fluid from the vessel 226 is introduced into the receiving end 218 of the adapter portion 130 and guided by the adapter channel 216 and the inner channel 204 to the exit end 220 of the body portion 110. As the exit end 220 of the body portion 110 is beneath the patient's skin 224, the fluid is released beneath the patient's skin 224. In some cases, fluid from the vessel 226 can be propelled from the vessel 226 and/or through the medical cannula 100 by a pump (e.g., a syringe pump or an electronic pump), or by some other device that applies pressure or suction.

In the example shown in FIG. 2B, the medical cannula 100 has not been damaged during operation. For instance, the body portion 110 has been inserted into the patient's body 222 in such a way that the inner wall 202 and the outer wall 206 remain straight and unbent. Thus, the inner channel 204 is not obstructed, and fluid can freely flow from the vessel 226 into the patient's body.

However, during use, the medical cannula 100 may become damaged. For example, in some cases, the medical cannula may bend or kink during use, which may obstruct the inner channel 204 and restrict the free flow of fluid into the patient.

Figure 3A:
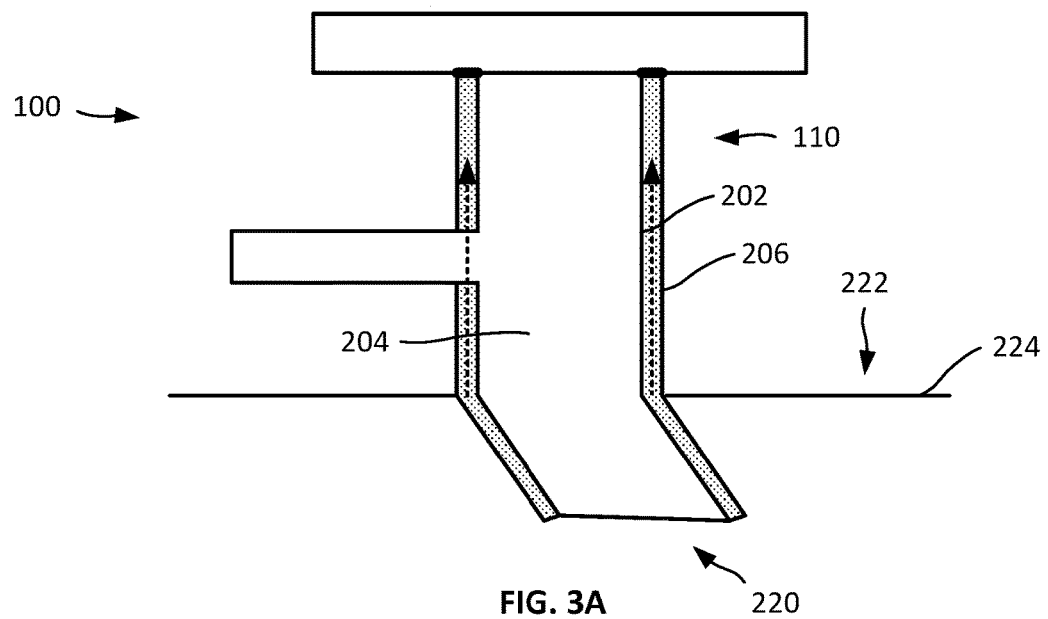
FIGS. 3A-3C are diagrams depicting the use of an example medical cannula that has been damaged during use.

To illustrate, FIG. 3A shows the medical cannula 100 inserted into a patient's body 222. As with the example shown in FIG. 2B, the medical cannula 100 can be inserted by pressing the medical cannula 100 against the patient's body 222, such that the exit end 220 of the body portion 110 pierces the patient's skin 224. However, in this example, the inner wall 202 and the outer wall 206 have been bent during insertion (e.g., due to the exit end 220 being deflected by the patient's skin 224 and/or structures below). Thus, the inner channel 204 is also bent. The bending of the inner wall 202 and the outer wall 206 increases the fluid pressure within the outer channel 208 (e.g., due to a decrease in the size of the outer channel 208 as a result of the bending).

Figure 3B:
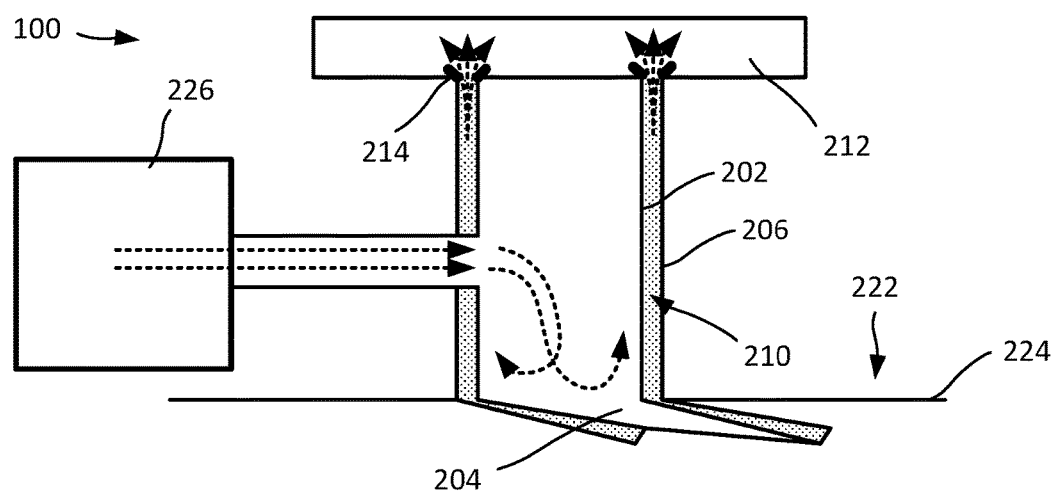

As shown in FIG. 3B, as the medical cannula 100 is further pressed against the patient's body 224, the inner wall 202 and the outer wall 206 increasingly bend. As a result, the inner channel 204 is crimped and becomes obstructed, thereby impeding the flow of fluid from the vessel 226 into the patient. In addition, the fluid pressure within the outer channel 208 is further increased (e.g., due to further decrease in the size of the outer channel 208 as a result of the bending). If the fluid pressure becomes sufficiently high, the frangible membrane 214 ruptures, releasing the indicator substance 210 into the indicator channel 212.

Figure 3C:
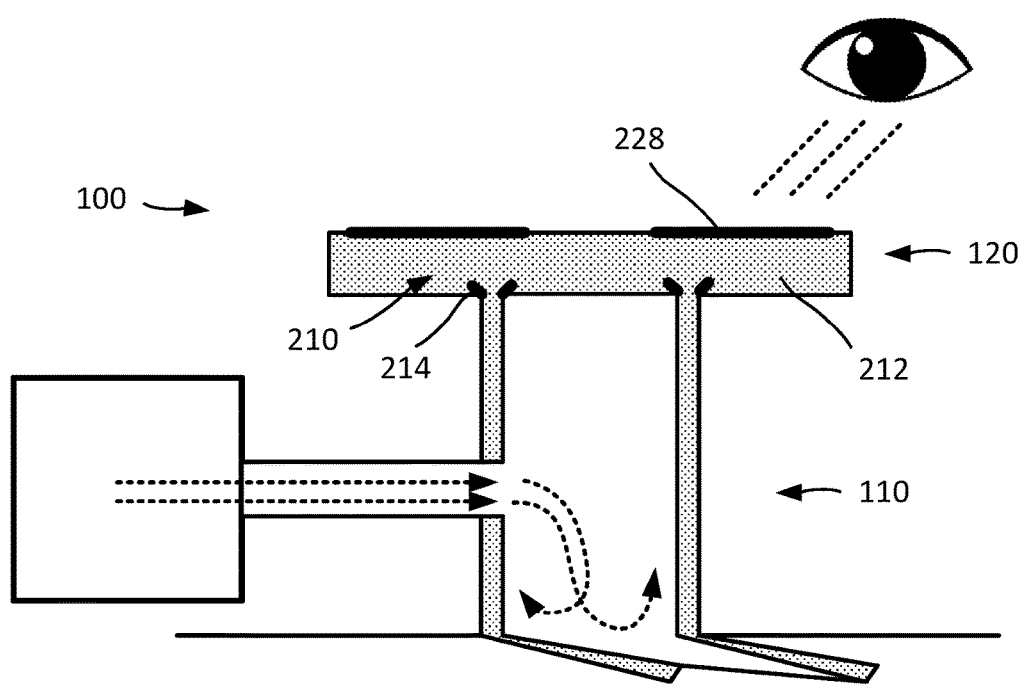

As shown in FIG. 3C, the release of the indicator substance 210 into the indicator channel 212 can be visually observed by a user. For example, the indicator portion 120 can include one or more transparent or translucent surfaces 228 that enable the user to view the interior of the indicator channel 212. Upon the rupture of the frangible membrane 214, the user observes a change in color within the indicator channel 212 (due to the introduction of the indicator substance 210 into the indicator channel 212). Based on this observation, the user ascertains that the body portion 110 has been bent or kinked, and that the medical cannula 100 is damaged. Accordingly, the user can replace the damaged medical cannula 100 (e.g., by removing the medical cannula 100 and reinserting a new or repaired medical cannula 100).

The release of the indicator substance 210 into the indicator channel 212 can be made more conspicuous in various ways. For example, the indicator channel can be initially empty (e.g., filled with air or in a state of vacuum), and the interior surface of the indicator channel 212 can have a color that it different than that of the indicator substance 210. Thus, when the indicator substance 210 is released in the indicator channel 212, the indicator substance 210 is readily observable by a change in color. To illustrate, the interior of the indicator channel 212 can be white, and the indicator substance 210 can be blue. Thus, the interior of the indicator channel 212 appears white when the medical cannula 100 is undamaged, and appears blue when the medical cannula 100 is bent or kinked.

As another example, the interior of the indicator channel 212 can contain a liquid having a color that it different than that of the indicator substance 210. Thus, when the indicator substance 210 is released in the indicator channel 212, the indicator substance is readily observable by a change in color. To illustrate, the indicator channel 212 contain a liquid having a clear color, and the indicator substance 210 can be black. Thus, the liquid in the indicator channel 212 appears clear when the medical cannula 100 is undamaged, and appears black when the medical cannula 100 is bent or kinked.

As another example, the interior of the indicator channel 212 can contain a fluid-sensitive material, such as a paper, sponge, or other material that changes color when contacted by a fluid. Thus, when the indicator substance 210 is released in the indicator channel 212, the indicator substance is readily observable by a change in color. To illustrate, the indicator channel 212 contain a fluid-sensitive material having a white color when dry, and a red color when wet (e.g., when it comes into contact with the indicator substance 210). Thus, the material in the indicator channel 212 appears white when the medical cannula 100 is undamaged, and appears red when the medical cannula 100 is bent or kinked.

Although example combinations of colors are described above, these are merely illustrative examples. In practice, any combination of colors can be used to visually indicate the condition of the medical cannula 100.

Although FIGS. 3A-3C show an example usage in which a medical cannula 100 is bent or kinked beneath the surface of a patient's skin, this need not be the case. For example, in some cases, a medical cannula 100 can bend or kink at a point above the surface of the patient's skin, such that the tip of the medical cannula 100 does not pierce the patient's skin at all. As another example, in some cases, a medical cannula 100 can bend at multiple points, including one or more points above the surface of the patient' s skin and one or more points beneath the surface of the patient's skin.

Further, although FIG. 3B shows the frangible membrane 214 rupturing when the inner wall 202 and outer wall 206 experience a particular degree of bending, this is merely an illustrative example. In practice, the frangible membrane 214 can be configured such that it ruptures when the inner wall 202 and outer wall 206 experience any specified degree of bending. For example, the frangible membrane 214 can be designed such that it ruptures if the inner wall 202 and/or the outer wall 206 experience any bending at all. As another example, the frangible membrane 214 can be designed such that it ruptures only if the inner wall 202 and/or the outer wall 206 experiences a degree of bending sufficient to obstruct the inner channel 204. In some cases, this can be achieved by configuring the frangible membrane 214 such that it ruptures in response to a pre-defined fluid pressure within the outer channel 208.

Figure 4A:
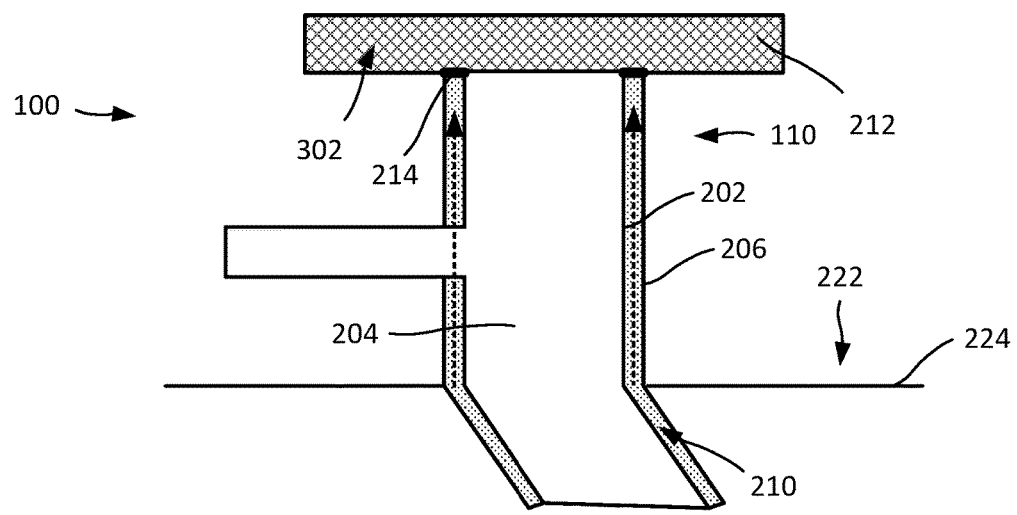
FIGS. 4A-4C are diagrams depicting the use of another example medical cannula that has been damaged during use.

In some cases, a medical cannula 100 can provide a visual indication of damage through a chemical reaction between two solutions. To illustrate, FIG. 4A shows the medical cannula 100 inserted into a patient's body 222. In this example, the indicator channel 212 contains a chemically reactive substance 302 that produces in a visually discernable chemical reaction when combined with the indicator substance 210 contained within the outer channel 208. The chemically reactive substance 302 and the indicator substance 210 are separated by the frangible membrane 214.

As with the example shown in FIG. 3A, the medical cannula 100 can be inserted by pressing the medical cannula 100 against the patient's body 222, such that the exit end 220 of the body portion 110 pierces the patient's skin 224. Similarly, in this example, the inner wall 202 and the outer wall 206 have been bent during insertion (e.g., due to the exit end 220 being deflected by the patient's skin 224 and/or structures below). Thus, the inner channel 204 is also bent. The bending of the inner wall 202 and the outer wall 206 increases the fluid pressure within the outer channel 208 (e.g., due to a decrease in the size of the outer channel 208 as a result of the bending).

Figure 4B:
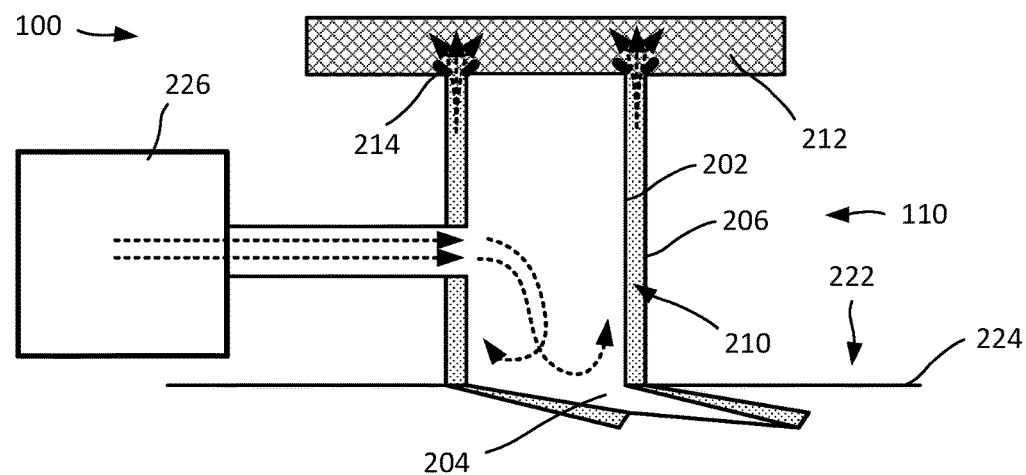

As shown in FIG. 4B, as the medical cannula 100 is further pressed against the patient's body 224, the inner wall 202 and the outer wall 206 increasingly bend. As a result, the inner channel 204 is crimped and becomes obstructed, thereby impeding the flow of fluid from the vessel 226 into the patient. In addition, the fluid pressure within the outer channel 208 is further increased (e.g., due to further decrease in the size of the outer channel 208 as a result of the bending). If the fluid pressure becomes sufficiently high, the frangible membrane 214 ruptures, releasing the indicator substance 210 into the indicator channel 212.

Figure 4C:
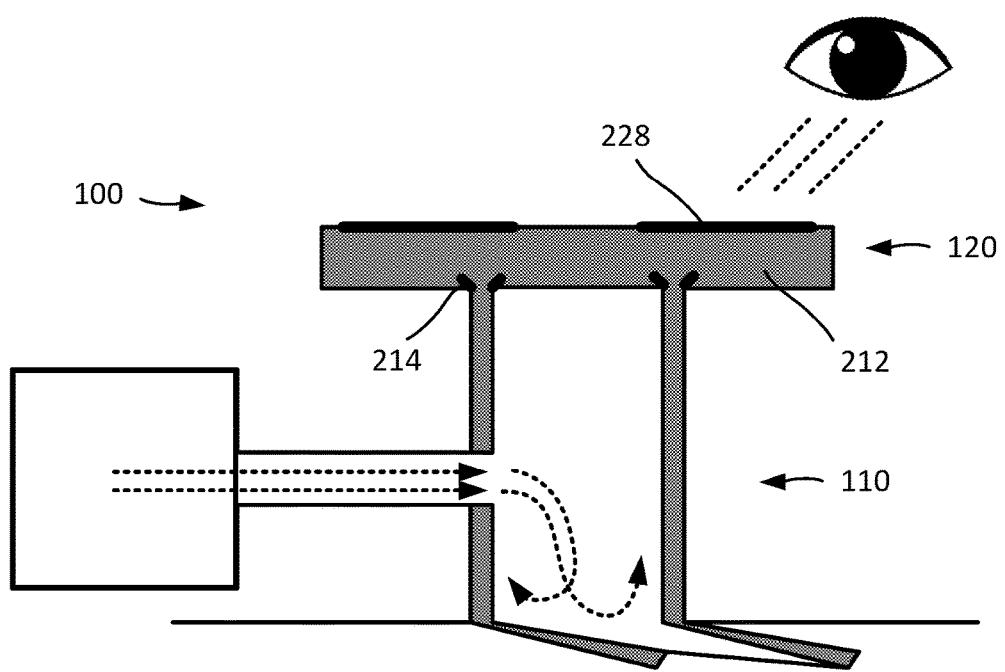

As shown in FIG. 4C, the release of the indicator substance 210 into the indicator channel 212 causes a chemical reaction with the chemically reactive substance 302 (depicted by the change of shading of the indicator channel 212). The chemical reaction between the indicator substance 210 and the chemically reactive substance 302 can be visually observed by a user. For example, the chemical reaction can result in a change of color (e.g., from a clear color to a red color), a change in clarity (e.g., through the creation of a precipitate), a change in photoluminescence, or a change in any other visually discernable property of the combined substances.

Further, in a similar manner as shown in FIG. 3C, the indicator portion 120 can include one or more transparent or translucent surfaces 228 that enable the user to view the interior of the indicator channel 212. Upon the rupture of the frangible membrane 214, the user observes the chemical reaction within the indicator channel 212 (due to the combination of the indicator substance 210 and the chemically reaction substance 302). Based on this observation, the user ascertains that the body portion 110 has been bent or kinked, and that the medical cannula 100 is damaged. Accordingly, the user can replace the damaged medical cannula 100 (e.g., by removing the medical cannula 100 and reinserting a new or repaired medical cannula 100).

Figure 5A:
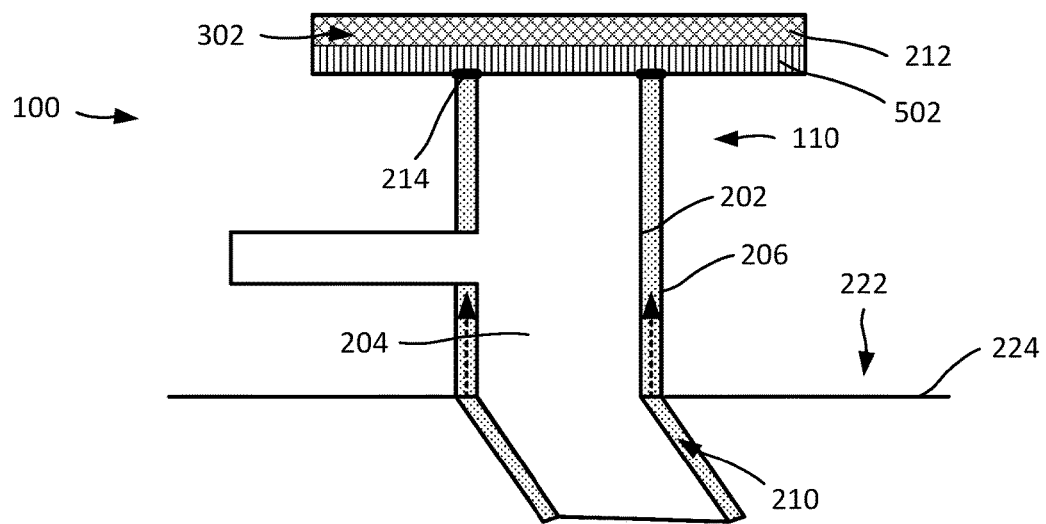
FIGS. 5A-5C are diagrams depicting the use of another example medical cannula that has been damaged during use.

In some cases, a medical cannula 100 can also include an interface material within the indicator channel 212 that further separates the contents of the outer channel 208 from the indicator channel 212. To illustrate, FIG. 5A shows the medical cannula 100 inserted into a patient's body 222. As with the example shown in FIG. 4A, the indicator channel 212 contains chemically reactive substance 302 that produces in a visually discernable chemical reaction when combined with the indicator substance 210 contained within the outer channel 208. The chemically reactive substance 302 and the indicator substance 210 are separated by the frangible membrane 214 and by an interface material 502. The interface material 502 is porous or semi-porous, such that fluids can permeate or diffuse through it. As an example, the interface material 502 can be a sponge, a paper, a fibrous material, a matrix material, or some other porous or semi-porous material.

In some cases, the interface material 502 can be directionally dependent, such that fluids can only permeate or diffuse through it in substantially one direction (e.g., in a direction from the outer channel 208 towards the indicator channel 212, but not in the opposite direction). In some cases, the interface material 502 can have diffusive properties that are dependent on fluid type or particle size, such that only particular types of fluids and/or particular sized particles can substantially permeate or diffuse through it (e.g., allowing for the diffusion of the indicator substance 210 across it, but not the diffusion of the chemically reactive substance 302).

As with the example shown in FIG. 4A, the medical cannula 100 can be inserted by pressing the medical cannula 110 against the patient's body 222, such that the exit end 220 of the body portion 110 pierces the patient's skin 224. Similarly, in this example, the inner wall 202 and the outer wall 206 have been bent during insertion (e.g., due to the exit end 220 being deflected by the patient's skin 224 and/or structures below). Thus, the inner channel 204 is also bent. The bending of the inner wall 202 and the outer wall 206 increases the fluid pressure within the outer channel 208 (e.g., due to a decrease in the size of the outer channel 208 as a result of the bending).

Figure 5B:
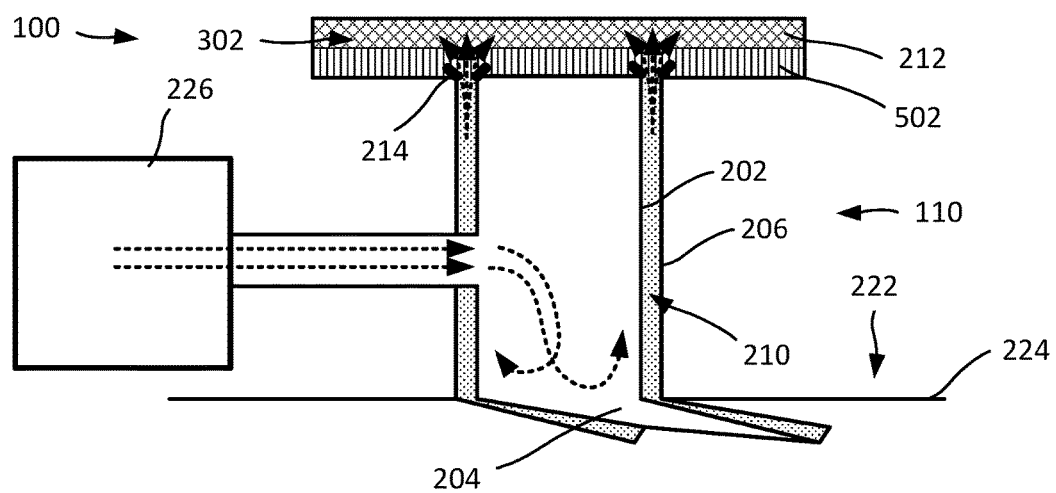

As shown in FIG. 5B, as the medical cannula 100 is further pressed against the patient's body 224, the inner wall 202 and the outer wall 206 increasingly bend. As a result, the inner channel 204 is crimped and becomes obstructed, thereby impeding the flow of fluid from the vessel 226 into the patient. In addition, the fluid pressure within the outer channel 208 is further increased (e.g., due to further decrease in the size of the outer channel 208 as a result of the bending). If the fluid pressure becomes sufficiently high, the frangible membrane 214 ruptures, releasing the indicator substance 210 into the interface material 502.

Figure 5C:
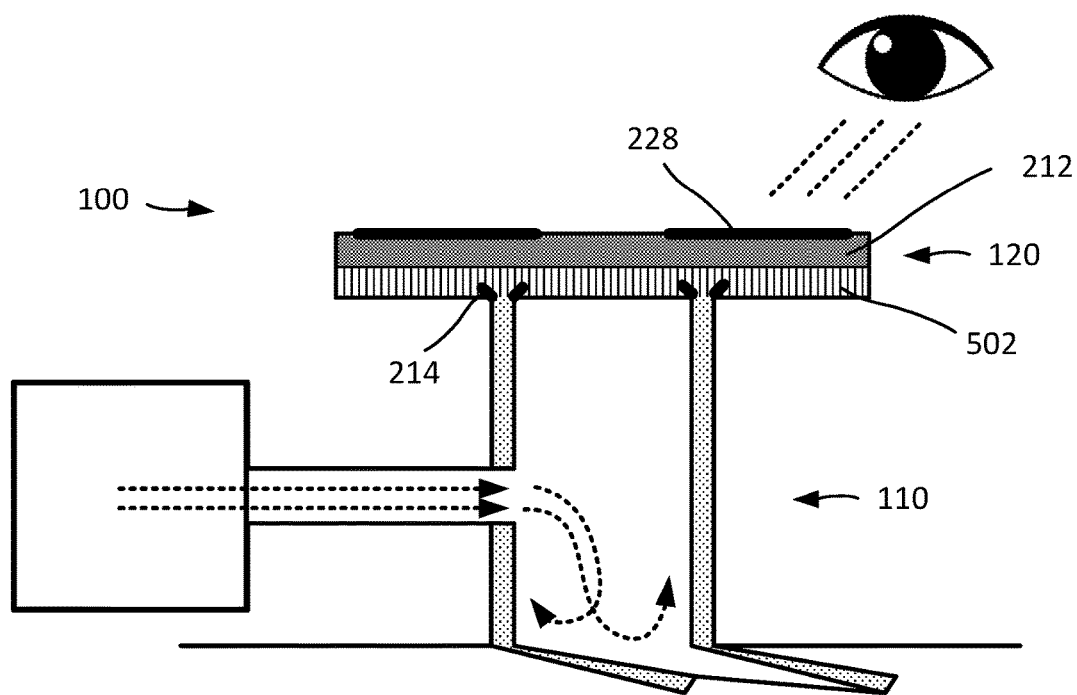

As shown in FIG. 5C, after the indicator substance 210 is released into the interface material 502, the indicator substance 210 diffuses through the interface material 502 and mixes with the chemically reactive substance 302. This results in a chemical reaction with the chemically reactive substance 302 (depicted by the change of shading of the upper portion of the indicator channel 212). The chemical reaction between the indicator substance 210 and the chemically reactive substance 302 can be visually observed by a user. For example, the chemical reaction can result in a change of color (e.g., from a clear color to a red color), a change in clarity (e.g., through the creation of a precipitate), a change in photoluminescence, or a change in any other visually discernable property of the combined substances.

Further, in a similar manner as shown in FIG. 4C, the indicator portion 120 can include one or more transparent or translucent surfaces 228 that enable the user to view the interior of the indicator channel 212. Upon the rupture of the frangible membrane 214, the user observes the chemical reaction within the indicator channel 212 (due to the combination of the indicator substance 210 and the chemically reaction substance 302). Based on this observation, the user ascertains that the body portion 110 has been bent or kinked, and that the medical cannula 100 is damaged. Accordingly, the user can replace the damaged medical cannula 100 (e.g., by removing the medical cannula 100 and reinserting a new or repaired medical cannula 100).

As described herein, a medical cannula can provide a visual indication when it is damaged. However, a medical cannula can also provide other indications when it is damaged, such as tactile feedback. This can be useful, for example, as it enables patients having impaired vision to ascertain when the medical cannula has been damaged.

Figure 6A:
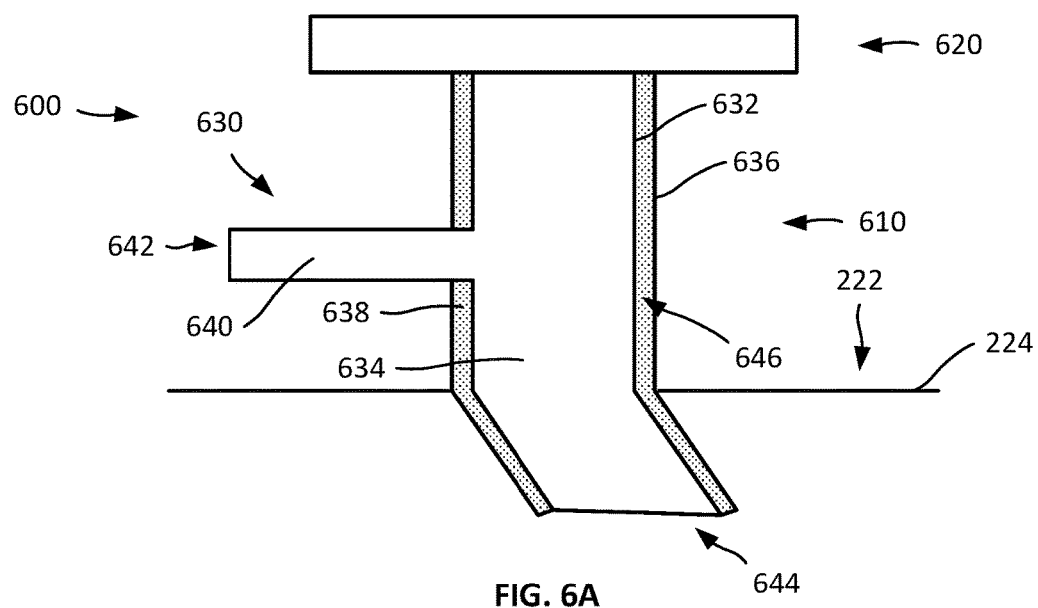
FIGS. 6A and 6B are diagrams depicting the use of another example medical cannula that has been damaged during use.

To illustrate, FIG. 6A shows the medical cannula 600 inserted into a patient's body 222. The medical cannula 600 includes a body portion 610, an upper portion 620, and an adapter portion 630. The body portion 610 and the adapter portion 630 are generally similar the body portion 110 and the adapter portion 130 described with respect to FIGS. 1 and 2A.

For example, the body portion 610 is generally tubular in shape. The body portion 610 includes a tubular inner wall 632 that defines an inner channel 634. The body portion also includes a tubular outer wall 636 that encircles the inner wall 632, such that an annular outer channel 638 is defined between the inner wall 632 and the outer wall 636. The inner channel 634 and the outer channel 638 are in fluid isolation with respect to one another, such that the contents of the inner channel 634 and the outer channel 638 do not mix.

Similarly, the adapter portion 630 protrudes from the body portion 610, and defines an adapter channel 640 that is in fluid communication with the inner channel 634. Fluids introduced into a receiving end 642 of the adapter portion 630 are guided to the exit end 644 of the body portion 610.

In this example, however, the outer channel 608 contains an indicator substance 646 that induces a tactile sensation when applied to the patient's body. As an example, the indicator substance 646 can be a mild irritant (e.g., a mildly acidic solution) that causes a perceptible sensation (e.g., a tingling or warm sensation) when applied to the patient's body.

When the medical cannula 600 is undamaged, the indicator substance 646 is securely contained within the outer channel 638. Thus, the indicator substance 646 does not induce a tactile sensitive in the body's body.

However, during use, the medical cannula 600 may become damaged. To illustrate, as shown in FIG. 6A, the inner wall 632 and the outer wall 636 have been bent during insertion (e.g., due to the exit end 644 being deflected by the patient's skin 224 and/or structures below). Thus, the inner channel 634 is also bent. The bending of the inner wall 632 and the outer wall 636 increases the fluid pressure within the outer channel 638 (e.g., due to a decrease in the size of the outer channel 638 as a result of the bending).

Figure 6B:
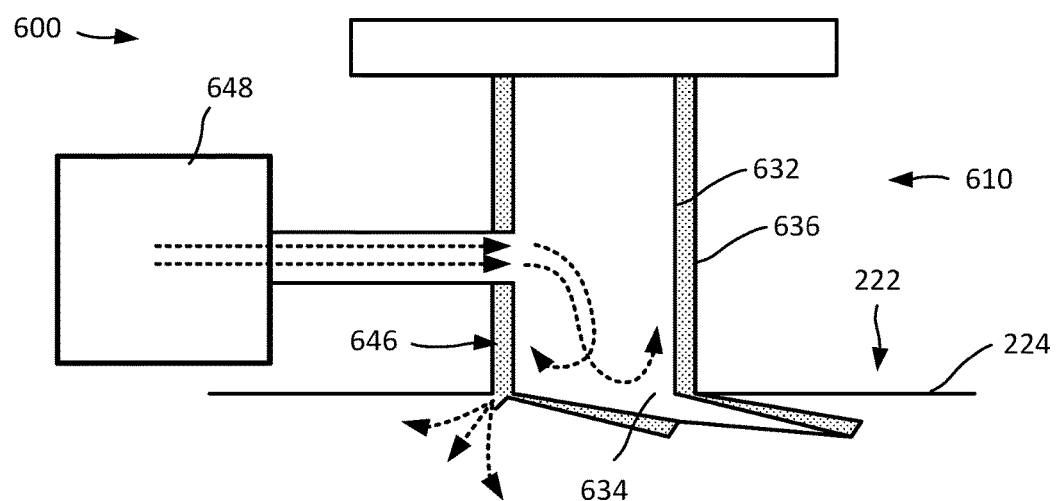

As shown in FIG. 6B, as the medical cannula 600 is further pressed against the patient's body 222, the inner wall 632 and the outer wall 636 increasingly bend. As a result, the inner channel 634 is crimped and becomes obstructed, thereby impeding the flow of fluid from a vessel 648 into the patient. In addition, the fluid pressure within the outer channel 638 is further increased (e.g., due to further decrease in the size of the outer channel 638 as a result of the bending). If the fluid pressure becomes sufficiently high, the outer wall 636 ruptures, releasing the indicator substance 646 into the patient's body 222. The release of the indicator substance 646 induces a tactile sensation (e.g., a mild tingling or warm sensation at or around the site of insertion). Based on this sensation, the user ascertains that the body portion 610 has been bent or kinked, and that the medical cannula 600 is damaged. Accordingly, the user can replace the damaged medical cannula 600 (e.g., by removing the medical cannula 600 and reinserting a new or repaired medical cannula 600).

Although FIG. 6B shows the outer wall 636 rupturing when it experiences a particular degree of bending, this is merely an illustrative example. In practice, the outer wall 636 can be configured such that it ruptures when it experiences any specified degree of bending. For example, the outer wall 636 can be designed such that it ruptures it experiences any bending at all. As another example, the outer wall 636 can be designed such that it ruptures only if it experiences a degree of bending sufficient to obstruct the inner channel 634. In some cases, this can be achieved by configuring the outer wall 636 such that it ruptures in response to a pre-defined fluid pressure within the outer channel 638.

Figure 7A:
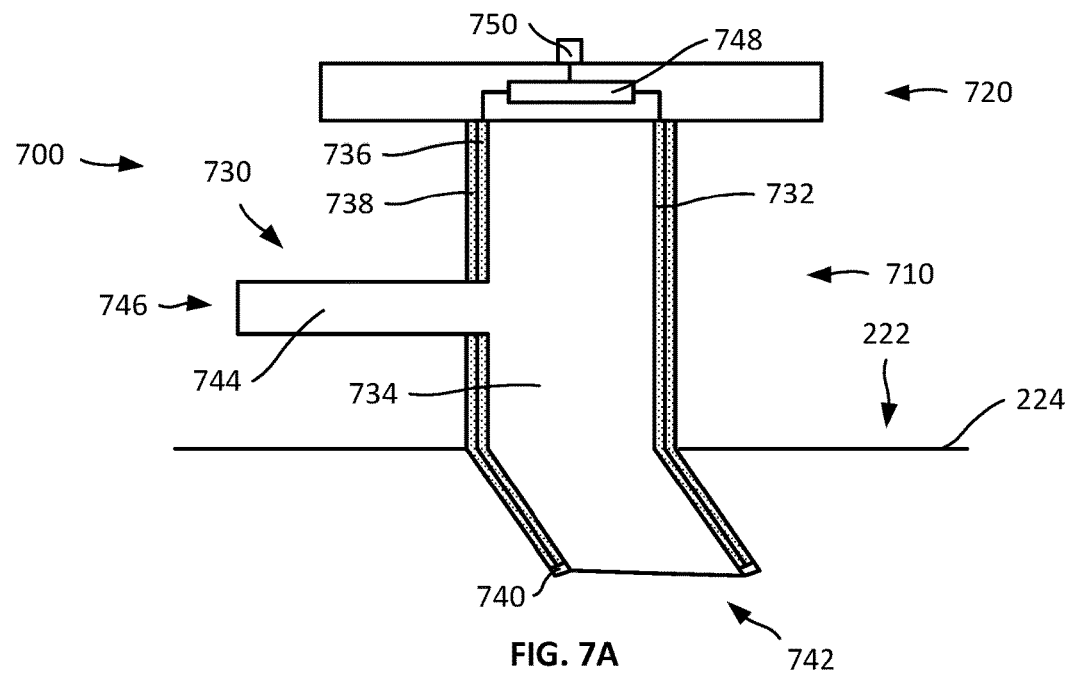
FIGS. 7A and 7B are diagrams depicting the use of another example medical cannula that has been damaged during use.

In some cases, a medical cannula can provide an electronic indication when it is damaged. To illustrate, FIG. 7A shows the medical cannula 700 inserted into a patient's body 222. The medical cannula 700 includes a body portion 710, an indicator portion 720, and an adapter portion 730.

The body portion 710 is generally tubular in shape. The body portion 710 includes a tubular wall 732 that defines an inner channel 734. The body portion also includes an inner layer 736 affixed to the wall 732, and an outer layer 738 affixed to the inner layer 736. The inner layer 736 is substantially enclosed by the outer layer 738, such that it is not exposed on the exterior of the medical cannula 700. The body portion 710 can also include an annular cap 740 that further covers the inner layer 736 at the exit end 742 of the body portion 710.

The inner layer 736 generates an electrical response when placed in contact with particular types of fluids. As an example, the inner layer 736 can generate an electrical current when placed in contact with the interstitial fluid of the body. In some cases, the electrical current can be induced due to a chemical interaction between the interstitial fluid and material of the inner layer 736.

The outer layer 738 shields the inner layer 736, such that the inner layer 736 is not exposed to the external environment. As a result, the inner layer 736 does not generate an electrical response (e.g., no electrical current is induced through the inner layer 736). In some cases, the outer layer 738 can be constructed from a water-resistant material, such that fluids cannot permeate through the outer layer 738 and come into contact with the inner layer 736.

The adapter portion 730 protrudes from the body portion 710, and defines an adapter channel 744 that is in fluid communication with the inner channel 734. Fluids introduced into a receiving end 746 of the adapter portion 730 are guided to the exit end 742 of the body portion 710.

The indicator portion 720 is positioned above the body portion 710 and includes a control module 748 and an indicator 750. The control module 748 is electrically coupled to the inner layer 736, and is configured to detect electrical current flowing through the inner layer 736. The control module 748 is also electrically coupled to an indicator 750, and is configured to activate the indicator element 750 when an electrical current is detected in the inner layer 736. The indicator can include one or more components capable of generating visual indications (e.g., light emitting didoes, liquid crystal displays, or other such components), one or more components capable of generating tactile indications (e.g., vibration motors), and/or one or more components capable of generating auditory indications (e.g., audio speakers). In some cases, the control module 748 can include an internal power supply (e.g., a battery) for powering the control module 748 and/or the indicator 750. In some cases, the control module 748 can be electrically coupled to an external power supply (e.g., an external battery, an electrical grid, or an external electrical device) for powering the control module 748 and/or the indicator 750.

In the example shown in FIG. 7A, the wall 732 has been bent during insertion (e.g., due to the exit end 742 being deflected by the patient's skin 224 and/or structures below), causing a corresponding bend in the inner layer 736 and outer layer 738. The inner channel 734 is also bent as a result.

However, in this configuration, the outer layer 738 is still intact, and is shielding the inner layer 736 such that the inner layer 736 is not exposed to the external environment. As a result, the inner layer 736 does not generate an electrical response (e.g., no electrical current is induced through the inner layer 736). Correspondingly, the control module 748 does not detect any electrical current in the inner layer 736, and does not activate the indicator element 750.

Figure 7B:
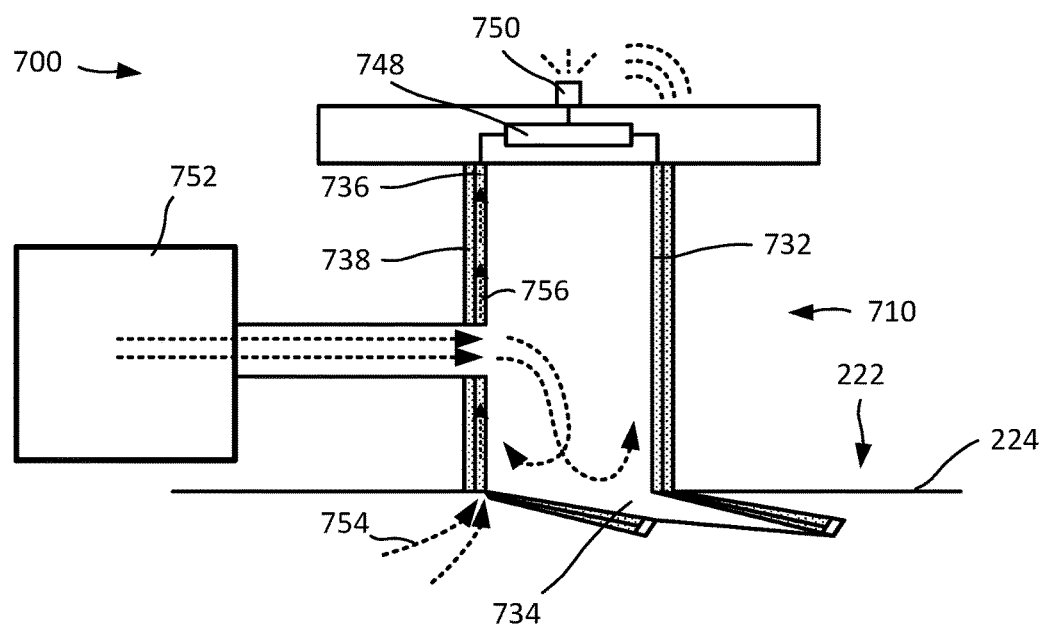

As shown in FIG. 7B, as the medical cannula 700 is further pressed against the patient's body 224, the wall 732, the inner layer 736, and the outer layer 738 increasingly bend. As a result, the inner channel 734 is crimped and becomes obstructed, thereby impeding the flow of fluid from a vessel 752 into the patient.

Further, when the outer layer 738 is bent to a sufficient degree, the outer layer 738 ruptures at its bending point and exposes the inner layer 736 to the external environment. As a result, the inner layer 736 comes into contact with the interstitial fluid of the body (represented by arrows 754), and generates an electrical response (e.g., an electrical current 756 across the inner layer 736). Correspondingly, the control module 748 detects the induced electrical current in the inner layer 736, and activates the indicator element 750.

The user observes the activated indicator element 750 (e.g., by seeing, hearing, and/or feeling an indication generated by the indicator element 750). Based on this observation, the user ascertains that the body portion 710 has been bent or kinked, and that the medical cannula 700 is damaged. Accordingly, the user can replace the damaged medical cannula 700 (e.g., by removing the medical cannula 700 and reinserting a new or repaired medical cannula 700).

In some cases, upon detecting a current in the inner layer 736, the control module 748 can transmit an electronic message to a computing device. For example, the control module 748 can include a wireless transceiver, and the wireless transceiver can transmit an electronic message across a communications network (e.g., a Wi-Fi network, a Bluetooth network, a cellular data network, or any other network) to a computing device (e.g., a server computer, a desktop computer, a notebook computer, a smartphone, a tablet computer, a pager, a wearable computer, an electronic monitoring device, or any other device capable of receiving data from a communications network). In response, the computing device generates a notification message to a user (e.g., a visual, auditory, and/or tactile notification) to inform the user that the medical cannula 700 has been damaged. In some cases, the control module 748 can transmit the electronic message either instead of or in addition to activating the indicator element 750.

Figure 8A:
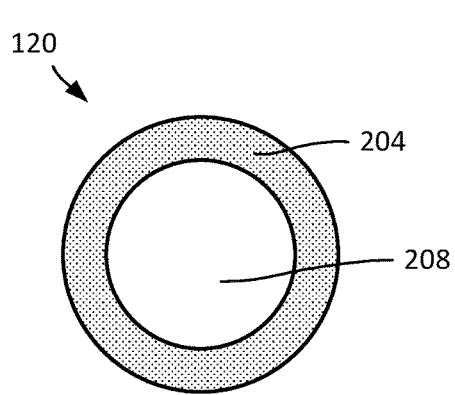
FIGS. 8A and 8B are diagrams of example body portions of an medical cannula.

As described herein, the body portion of a medical cannula can be generally tubular in shape. As an example, FIG. 8A shows a cross-section of the body portion 110 (e.g., viewed from a plane orthogonal of the axis of extension 140). The inner channel 204 has an approximately circular cross-section, and an outer channel 208 has an approximately annular cross-section.

Figure 8B:
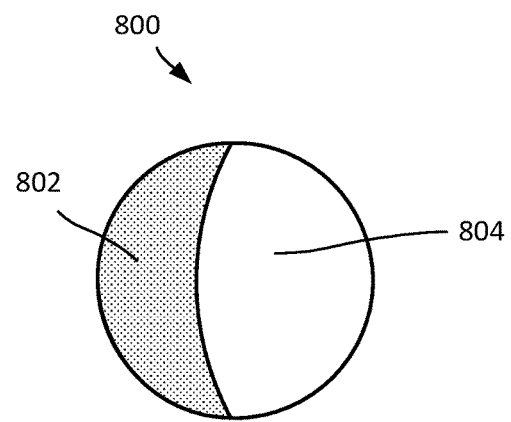

However, in practice, the channels can have any shape and arrangement respect to one another. For example, FIG. 8B shows a cross-section of another body portion 800. The body portion 800 includes a first channel 802 having a crescent-shaped cross-section, and a second channel 804 having a generally circular cross-section (with the crescent-shaped removed). The first channel 802 can contain an indicator solution (e.g., in a similar manner as the outer channels described herein), and the second channel 804 can be used to guide the flow of fluid from a vessel into a patient's body (e.g., in a similar manner as the inner channels described herein). Thus, some implementations of the medical cannula need not have "inner" and "outer" channels, and instead can have other arrangements of channels to provide the described features. Other shapes and arrangements of channels are also possible, depending on the implementation. Further, a medical cannula can include any number of channels (e.g., one or more channels containing an indicator solution, and one or more channels for guiding fluid into a patient), depending on the implementation.

In the examples shown in FIGS. 1-8, a medical cannula is attached to an external vessel, and the contents of the vessel are delivered from the vessel to the patient's body. This vessel can be, for example, a container (e.g., a bottle, a vial, a capsule, a pouch, or some other container for holding fluid) or a connector to a container (e.g., a tube, IV line, a pipe, or any other connector for transporting fluid). The container can be filled with a therapeutic substance (e.g., an insulin solution, a saline solution, or any other therapeutic substance).

Figure 9:
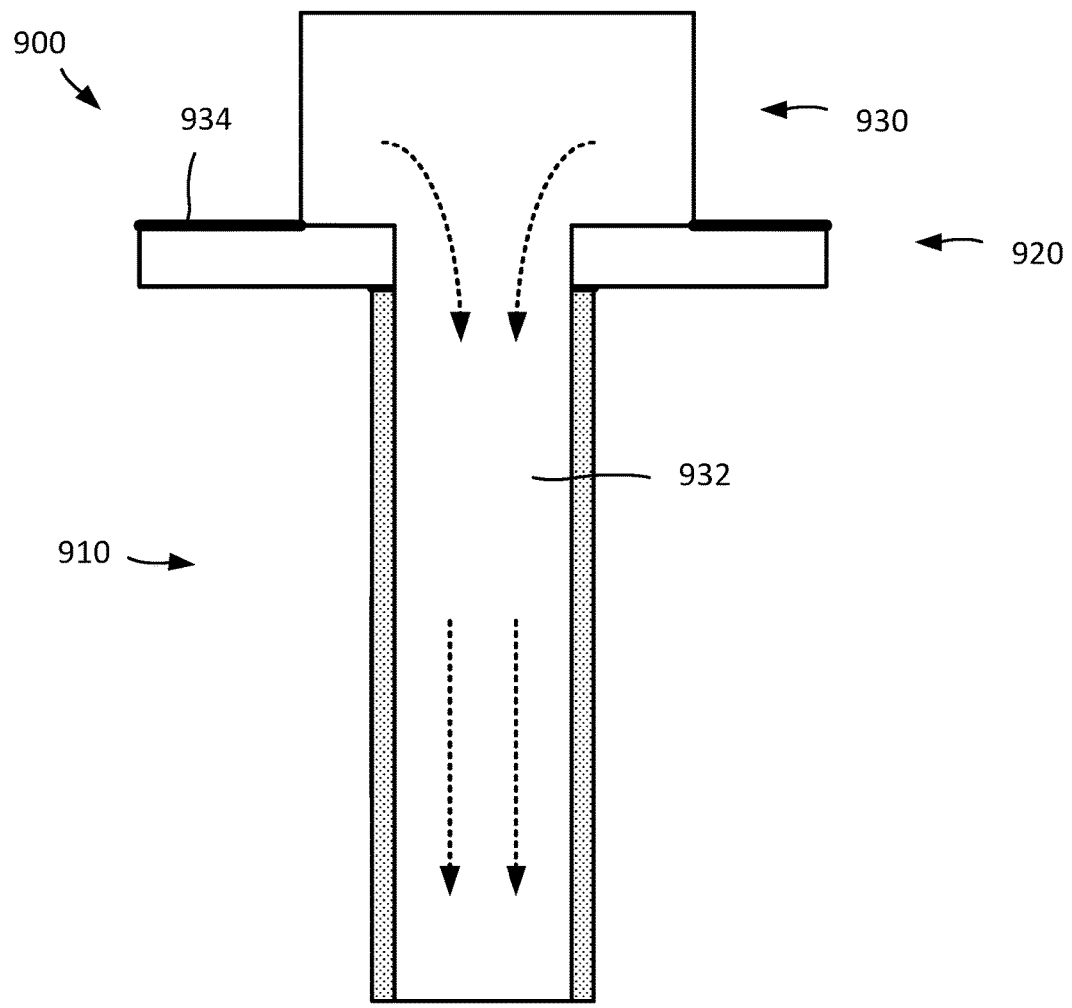
FIG. 9 is a diagram of another example medical cannula.

However, in some cases, a vessel can be provided as a part of the medical cannula itself. For example, as shown in FIG. 9, a medical cannula 900 can include a body portion 910 and an indicator portion 920. The body portion 910 and the indicator portion 920 can be generally similar the other body portions and the indicator portions described herein (e.g., the body portion 110 and the indicator portion 120 shown in FIGS. 1-3). However, in this example, the medical cannula includes a reservoir 930 in fluid communication with the inner channel 932 of the medical cannula 900. Thus, when the medical 900 is inserted into the patient's body, the contents of the reservoir 930 are guided by the inner channel 932 into the patient. The reservoir 930 is implemented as a part of the medical cannula 900 itself, such that the user does not need to attach a separate vessel prior to use.

In a similar manner as described with respect to FIGS. 1-3, the indicator portion 920 allows a user to visually discern whether the medical cannula 900 has been damaged (e.g., through transparent or translucent surfaces 934 enabling a user to view the release of an indicator substance into the indicator portion 920).

A medical cannula having an integrated reservoir can be implemented in combination with any of the indication mechanisms described herein. For example, a medical cannula having an integrated reservoir can include mechanisms that indicate damage through a chemical reaction (e.g., as shown in FIGS. 4A-4C and 5A-5C), mechanisms that indicate damage through tactile feedback (e.g., as shown in FIGS. 6A and 6B), and/or mechanisms that indicate damage electronically (e.g., as shown in FIGS. 7A and 7B).

Although example components and devices are shown in the accompanying drawings, it is understood that the components and devices have not been drawn to scale. For example, certain features may be enlarged relative to other features to better illustrate particular structures or functions. Further, certain features may be larger or smaller relative to other features than shown in the drawings, depending on the intended application. Thus, in practice, implementations of the components and devices described herein may have dimensions and proportions different than those shown in the drawings.

As an example, a medical cannula can include an inner channel having a diameter of approximately 1.0 mm (e.g., between 0.5 mm to 1.5 mm). As another example, a medical cannula can include an outer channel having a diameter of approximately 1.5 mm (e.g., between 1.0 mm and 2.0 mm). As another example, a medical cannula can include an indicator portion having a diameter of approximately 8.0 mm (e.g., between 7.0 mm and 9.0 mm). As another example, a medical cannula can include a body portion having a length of approximately 1.0 cm (e.g., between 0.5 cm and 1.5 cm) along its axis of extension. Other dimension are also possible, depending on the implementation.

As described herein, implementations of a medical cannula enable a user to visually ascertain whether a cannula has been bent or kinked during insertion or use. Although various examples of bending and kinking are depicted and described herein, these are merely illustrative examples. In some cases, a medical cannula can be considered bent or kinked when a degree of deflection of the medical cannula impacts, may impact, or is likely to impact the flow of therapeutic substance through the medical cannula to the patient. In practice, this degree of deflection can vary based on many factors, including the properties of the therapeutic substance, the dimensions of the medical cannula and its subcomponents (e.g., the body portion), the materials used to construct the medical cannula, among others. As examples, in some cases, this degree of deflection can be approximately 15°, 30°, 45°, 60°, 75°, 90°, 105°, 120°, 135°, 150°, 165°, 180°, or any other angle.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the control module 748 and/or the computing devices in communication with the control module 748 can be implemented using digital electronic circuitry, or in computer software, firmware, or hardware, or in combinations of one or more of them.

Some aspects of implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some aspects of implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks , and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, it will be understood that various modifications may be made without departing from the spirit and scope of the invention. Accordingly, other embodiments are within the scope of the following claims.

What is claimed is:

1. A medical device comprising:
    a body portion comprising:
        a tubular inner wall defining an inner channel; and
        a tubular outer wall encircling the inner wall, the outer wall defining an outer channel between the outer wall and the inner wall;
    an indicator substance disposed within the outer channel; and
    an indicator portion defining an indicator channel;
    wherein the body portion is configured to insert at least in part into a patient, and the indicator portion is configured to remain at least in part along an exterior of the patient when the body portion is inserted into the patient, and
    wherein the device is configured to transfer at least a portion of the indicator substance from the outer channel to the indicator channel when the body portion is bent.

2. The medical device of claim 1, wherein the outer channel and the indicator channel are separated by a frangible membrane, and wherein the frangible membrane is configured to rupture when the body portion is bent.

3. The medical device of claim 2, wherein the indicator channel and the outer channel are in fluid communication upon rupture of the frangible membrane.

4. The medical device of claim 1, wherein the indicator portion comprises a transparent or translucent surface, and wherein an interior of the indicator channel is visible through the transparent or translucent surface when the body portion is inserted into the patient.

5. The medical device of claim 1, wherein the indicator substance comprises a colored dye.

6. The medical device of claim 1, wherein the indicator channel contains a reactive substance, and wherein transferring at least the portion of the indicator substance from the outer channel to the indicator channel causes a reaction between the indicator substance and the reactive substance.

7. The medical device of claim 6, wherein the reaction causes the indicator substance to change color.

8. The device of claim 1, wherein the indicator portion is disposed along a first end of the outer channel.

9. The device of claim 1, wherein the indicator portion is disc shaped.

10. The medical device of claim 1, further comprising an adapter portion, wherein the adapter portion defines an access channel through the inner wall and the outer wall, wherein the access channel is in fluid communication with the inner channel.

11. The medical device of claim 10, wherein the adapter portion is configured to physically couple to a vessel containing a fluid, and wherein the device is configured to deliver the fluid from the vessel to the patient through the access channel and the inner channel.

12. The medical device of claim 11, wherein the fluid comprises insulin.

13. The medical device of claim 1, further comprising a reservoir containing a fluid, wherein the reservoir is in fluid communication with the inner channel.

14. The medical device of claim 13, wherein the fluid comprises insulin.

15. The medical device of claim 1, further comprising an interface material positioned within the indicator channel.

16. The medical device of claim 15, wherein the interface material is a sponge.

* * * * *